United States Patent
Bennett et al.

(10) Patent No.: US 6,372,492 B1
(45) Date of Patent: Apr. 16, 2002

(54) ANTISENSE MODULATION OF TALIN EXPRESSION

(75) Inventors: C. Frank Bennett; Lex M. Cowsert, both of Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/702,251

(22) Filed: Oct. 30, 2000

(51) Int. Cl.$^7$ .......................... C12N 15/00; C12Q 1/68; A61K 48/00

(52) U.S. Cl. .......................... 435/375; 435/6; 435/325; 435/366; 435/91.1; 536/23.1; 536/24.5; 536/25.3; 514/44

(58) Field of Search ................................ 514/44; 435/6, 435/325, 366, 375, 91.1; 536/23.1, 24.5, 25.3

(56) References Cited

U.S. PATENT DOCUMENTS

| | | | | |
|---|---|---|---|---|
| 5,801,154 A | * | 9/1998 | Baracchini et al. | 514/44 |
| 5,951,455 A | * | 9/1999 | Cowsert | 495/375 |

OTHER PUBLICATIONS

W. Michael Flanagan et al., Cellular penetration and antisense activity by a phenoxazine–substituted heptanucleotide, Research, pp. 1–5.*

Andrea D. Branch, A good antisense molecule is hard to find, TIBS 23—Feb. 1998, pp. 45–50.*

Albiges–Rizo et al., Down regulation of talin alters cell adhesion and the processing of the alpha 5 beta 1 integrin, *J. Cell. Sci.*, 1995, 108:3317–3329.

Beckerle et al., Activation–dependent redistribution of the adhesion plaque protein, talin, in intact human platelets, *J. Cell. Biol.*, 1989, 109:333–3346.

Beckerle et al., Demonstration of a relationship between talin and P235, a major substrate of the calcium–dependent protease in platelets, *J. Cell. Biochem.*, 1986, 30:259–270.

Beckerle et al., Talin: role at sites of cell–substratum adhesion, *Cell Motil. Cytoskeleton*, 1990, 16:7–13.

Betts et al., Paracrine regulation of talin mRNA expression by androgen in human prostate, *FEBS Lett.*, 1998, 434:66–70.

Bolton et al., Monoclonal antibodies recognizing the N– and C–terminal regions of talin disrupt actin stress fibers when microinjected into human fibroblasts, *Cell. Motil. Cytoskeleton*, 1997, 36:363–376.

Burridge et al., An interaction between vinculin and talin, *Nature*, 1984, 308:744–746.

Collier et al., Human platelet P235: a high Mr protein which restricts the length of actin filaments, *FEBS Lett.*, 1982, 143:205–210.

Collier et al., Purification and properties of human platelet P235. A high molecular weight protein substrate of endogenous calcium–activated protease(s), *J. Biol. Chem.*, 1982, 257:6937–6943.

Critchley et al., Integrin–mediated cell adhesion: the cytoskeletal connection, *Biochem. Soc. Symp.*, 1999, 65:79–99.

Frenette et al., Mechanical loading regulates expression of talin and its mRNA, which are concentrated at myotendinous junctions, *Am. J. Physiol.*, 1998, 275:C818–825.

Goldmann et al., Vinculin, talin and focal adhesions, *J. Muscle Res. Cell Motil.*, 1996, 17:1–5.

Goldmann et al., The effect of intact talin and talin tail fragment on actin filament dynamics and structure depends on pH and ionic strength, *Eur. J. Biochem.*, 1999, 260:439–445.

Horwitz et al., Interaction of plasma membrane fibronectin receptor with talin—a transmembrane linkage, *Nature*, 1986, 320:531–533.

Imanaka–Yoshida et al., Vinculin, Talin, Integrin alpha6beta1 and laminin can serve as components of attachment complex mediating contraction force transmission from cardiomycytes to extracellular matrix, *Cell Motil. Cytoskeleton*, 1999, 42:1–11.

Isenberg et al., Peptide–specific antibodies localize the major lipid binding sites of talin dimers to oppositely arrange N–terminal 47 kDa subdomains, *FEBS Lett.*, 1998, 426:165–170.

Knezevic et la., Direct binding of the platelet integrin alphaIIbbeta3 (GPIIb–IIIa) to talin. Evidence that interaction is mediated through the cytoplasmic domains of both alphaIIb and beta3, *J. Biol. Chem.*, 1996, 271:16416–16421.

Lin et al., N–terminal myosin–binding fragment of talin, *Biochem. Biophys. Res. Commun.*, 1998, 249:656–659.

Litchfield et al., Phosphorylation of the cytoskeleta protein talin by protein kinase C, *Biochem. Biophys. Res. Commun.*, 1986, 134:1276–1283.

Priddle et al., Disruption of the talin gene comprises focal adhesion assembly in undifferentiated but not differentiated embryonic stem cells, *J. Cell. Biol.*, 1998, 142:1121–1133.

Saitoh et al., Opening–up of liposomal membranes by talin, *Proc. Natl. Acad. Sci. U. S. A.*, 1998, 95:1026–1031.

Schmidt et al., Interaction of talin with actin: sensitive modulation of filament crosslinking activity, *Arch. Biochem. Biophys.*, 1999, 366:139–150.

Tidball et al., Talin at myotendinous junctions, *J. Cell. Biol.*, 1986, 103:1465–1472.

(List continued on next page.)

Primary Examiner—Andrew Wang
Assistant Examiner—M Schmidt
(74) Attorney, Agent, or Firm—Licata & Tyrrell P.C.

(57) ABSTRACT

Antisense compounds, compositions and methods are provided for modulating the expression of Talin. The compositions comprise antisense compounds, particularly antisense oligonucleotides, targeted to nucleic acids encoding Talin. Methods of using these compounds for modulation of Talin expression and for treatment of diseases associated with expression of Talin are provided.

26 Claims, No Drawings

OTHER PUBLICATIONS

Watters et al., Bistratene A causes phosphorylation of talin and redistribution of actin microfilaments in fibroblasts: possible role for PKC–delta, *Exp. Cell. Res.*, 1996, 229:327–335.

Zhang et al., Talin can crosslink actin filaments into both networks and bundles, *Biochem. Biophys. Res. Commun.*, 1996, 218:530–537.

* cited by examiner

SEQUENCE LISTING

<160> NUMBER OF SEQ ID NOS: 89

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                        20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                        20

<210> SEQ ID NO 3
<211> LENGTH: 8078
<212> TYPE: DNA
<213> ORGANISM: Homo sapiens
<220> FEATURE:
<221> NAME/KEY: CDS
<222> LOCATION: (127)..(7752)

<400> SEQUENCE: 3
aatataccaa gacgaaggag gcagccggac ccaggcgacc ccgagaatcg gcggggcgcg    60
ggccgcgggc ggggcgagag ccaggcagcg caggtatagc caggctggag aaaagaagct   120 gccacc atg gtt gca ctt tca ctg aag atc agc att ggg aat gtg gtg     168
       Met Val Ala Leu Ser Leu Lys Ile Ser Ile Gly Asn Val Val
         1               5                  10 aag acg atg cag ttt gag ccg tct acc atg gtg tac gac gcc tgc cgc    216
Lys Thr Met Gln Phe Glu Pro Ser Thr Met Val Tyr Asp Ala Cys Arg
 15                  20                  25                  30 atc att cgt gag cgg atc cca gag gcc cca gct ggt cct ccc agc gac    264
Ile Ile Arg Glu Arg Ile Pro Glu Ala Pro Ala Gly Pro Pro Ser Asp
                 35                  40                  45 ttt ggg ctc ttt ctg tca gat gat gac ccc aaa aag ggt ata tgg ctg    312
Phe Gly Leu Phe Leu Ser Asp Asp Asp Pro Lys Lys Gly Ile Trp Leu
             50                  55                  60 gag gct ggg aaa gct ttg gac tac tac atg ctc cga aat ggg gac act    360
Glu Ala Gly Lys Ala Leu Asp Tyr Tyr Met Leu Arg Asn Gly Asp Thr
         65                  70                  75 atg gag tac agg aag aaa cag aga ccc ctg aag atc cgt atg ctg gat    408
Met Glu Tyr Arg Lys Lys Gln Arg Pro Leu Lys Ile Arg Met Leu Asp
     80                  85                  90 gga act gtg aag acg atc atg gtg gat gac tct aag act gtc act gac    456
Gly Thr Val Lys Thr Ile Met Val Asp Asp Ser Lys Thr Val Thr Asp
 95                 100                 105                 110 atg ctc atg acc atc tgt gcc cgc att ggc atc acc aat cat gat gaa    504
Met Leu Met Thr Ile Cys Ala Arg Ile Gly Ile Thr Asn His Asp Glu
                115                 120                 125 tat tca ttg gtt cga gag ctg atg gaa gag aaa aag gag gaa ata aca    552
Tyr Ser Leu Val Arg Glu Leu Met Glu Glu Lys Lys Glu Glu Ile Thr
            130                 135                 140

```
ggt acc tta aga aag gac aag aca ttg ctg cga gat gaa aag aag atg      600
Gly Thr Leu Arg Lys Asp Lys Thr Leu Leu Arg Asp Glu Lys Lys Met
        145                 150                 155 gag aaa cta aag cag aaa ttg cac aca gat gat gag ttg aac tgg ctg      648
Glu Lys Leu Lys Gln Lys Leu His Thr Asp Asp Glu Leu Asn Trp Leu
160                 165                 170 gac cat ggt cgg aca ctg agg gag cag ggt gta gag gag cac gag acg      696
Asp His Gly Arg Thr Leu Arg Glu Gln Gly Val Glu Glu His Glu Thr
175                 180                 185                 190 ctg ctg ctg cgc agg aag ttc ttt tac tca gac cag aat gtg gat tcc      744
Leu Leu Leu Arg Arg Lys Phe Phe Tyr Ser Asp Gln Asn Val Asp Ser
            195                 200                 205 cgg gac cct gta cag ctg aac ctc ctg tat gtg cag gca cga gat gac      792
Arg Asp Pro Val Gln Leu Asn Leu Leu Tyr Val Gln Ala Arg Asp Asp
        210                 215                 220 atc ctg aat ggc tcc cac cct gtc tcc ttt gac aag gcc tgt gag ttt      840
Ile Leu Asn Gly Ser His Pro Val Ser Phe Asp Lys Ala Cys Glu Phe
                225                 230                 235 gct ggc ttc caa tgc cag atc cag ttt ggg ccc cac aat gag cag aag      888
Ala Gly Phe Gln Cys Gln Ile Gln Phe Gly Pro His Asn Glu Gln Lys
240                 245                 250 cac aag gct ggc ttc ctt gac ctg aag gac ttc ctg ccc aag gag tat      936
His Lys Ala Gly Phe Leu Asp Leu Lys Asp Phe Leu Pro Lys Glu Tyr
255                 260                 265                 270 gtg aag cag aag gga gag cgt aag atc ttc cag gca cac aag aat tgt      984
Val Lys Gln Lys Gly Glu Arg Lys Ile Phe Gln Ala His Lys Asn Cys
            275                 280                 285 ggg cag atg agt gag att gag gcc aag gtc cgc tac gtg aag cta gcc     1032
Gly Gln Met Ser Glu Ile Glu Ala Lys Val Arg Tyr Val Lys Leu Ala
        290                 295                 300 cgt tct ctc aag act tac ggt gtc tcc ttc ttc ctg gtg aag gaa aaa     1080
Arg Ser Leu Lys Thr Tyr Gly Val Ser Phe Phe Leu Val Lys Glu Lys
                305                 310                 315 atg aaa ggg aag aac aag cta gtg ccc agg ctt ctg ggc atc acc aag     1128
Met Lys Gly Lys Asn Lys Leu Val Pro Arg Leu Leu Gly Ile Thr Lys
320                 325                 330 gag tgt gtg atg cga gtg gat gag aag acc aag gaa gtg atc cag gag     1176
Glu Cys Val Met Arg Val Asp Glu Lys Thr Lys Glu Val Ile Gln Glu
335                 340                 345                 350 tgg aac ctc acc aac atc aaa cgc tgg gct gcg tct ccc aaa agc ttc     1224
Trp Asn Leu Thr Asn Ile Lys Arg Trp Ala Ala Ser Pro Lys Ser Phe
            355                 360                 365 acc ctg gat ttt gga gat tac caa gat ggc tat tac tca gta cag aca     1272
Thr Leu Asp Phe Gly Asp Tyr Gln Asp Gly Tyr Tyr Ser Val Gln Thr
        370                 375                 380 act gaa ggg gag cag att gca cag ctc att gcc ggc tac atc gat atc     1320
Thr Glu Gly Glu Gln Ile Ala Gln Leu Ile Ala Gly Tyr Ile Asp Ile
                385                 390                 395 atc ctg aag aag aaa aaa agc aag gat cac ttt ggg ctg gaa gga gat     1368
Ile Leu Lys Lys Lys Lys Ser Lys Asp His Phe Gly Leu Glu Gly Asp
400                 405                 410 gag gag tct act atg ctg gag gac tca gtg tcc ccc aaa aag tca aca     1416
Glu Glu Ser Thr Met Leu Glu Asp Ser Val Ser Pro Lys Lys Ser Thr
415                 420                 425                 430 gtc ctg cag cag caa tac aac cgg gtg ggg aaa gtg gag cat ggc tct     1464
Val Leu Gln Gln Gln Tyr Asn Arg Val Gly Lys Val Glu His Gly Ser
            435                 440                 445 gtg gcc ctg cct gcc atc atg cgc tct gga gcc tct ggt cct gag aat     1512
Val Ala Leu Pro Ala Ile Met Arg Ser Gly Ala Ser Gly Pro Glu Asn
        450                 455                 460
```

-continued

| | | |
|---|---|---|
| ttc cag gtg ggc agc atg ccc cct gcc cag cag cag att acc agc ggc<br>Phe Gln Val Gly Ser Met Pro Pro Ala Gln Gln Gln Ile Thr Ser Gly<br>           465                          470                      475 | 1560 | cag atg cac cga gga cac atg cct cct ctg act tca gcc cag cag gca         1608
Gln Met His Arg Gly His Met Pro Pro Leu Thr Ser Ala Gln Gln Ala
            480                 485                 490 ctc act gga acc att aac tcc agc atg cag gcc gtg cag gct gcc cag         1656
Leu Thr Gly Thr Ile Asn Ser Ser Met Gln Ala Val Gln Ala Ala Gln
495                 500                 505                 510 gcc acc ctg gat gac ttt gac act ctg ccg cct ctt ggc cag gat gct         1704
Ala Thr Leu Asp Asp Phe Asp Thr Leu Pro Pro Leu Gly Gln Asp Ala
                515                 520                 525 gcc tct aag gcc tgg cgt aaa aac aag atg gat gaa tca aag cat gag         1752
Ala Ser Lys Ala Trp Arg Lys Asn Lys Met Asp Glu Ser Lys His Glu
            530                 535                 540 atc cac tct cag gta gat gcc atc aca gct ggt act gcg tct gtg gtg         1800
Ile His Ser Gln Val Asp Ala Ile Thr Ala Gly Thr Ala Ser Val Val
        545                 550                 555 aac ctg aca gca ggg gac cct gct gag aca gac tat acc gca gtg ggc         1848
Asn Leu Thr Ala Gly Asp Pro Ala Glu Thr Asp Tyr Thr Ala Val Gly
560                 565                 570 tgt gca gtc acc aca atc tcc tcc aac ctg acg gag atg tcc cgt ggg         1896
Cys Ala Val Thr Thr Ile Ser Ser Asn Leu Thr Glu Met Ser Arg Gly
575                 580                 585                 590 gtg aag ctg ctg gct gcc ttg ctg gag gac gaa ggc ggc agt ggt cgg         1944
Val Lys Leu Leu Ala Ala Leu Leu Glu Asp Glu Gly Gly Ser Gly Arg
                595                 600                 605 ccc ctg ttg cag gca gca aag ggc ctt gcg gga gca gtg tca gaa ctg         1992
Pro Leu Leu Gln Ala Ala Lys Gly Leu Ala Gly Ala Val Ser Glu Leu
            610                 615                 620 ctg cgc agt gcc caa cca gcc agt gct gag ccc gtc cag aac ctg ctg         2040
Leu Arg Ser Ala Gln Pro Ala Ser Ala Glu Pro Arg Gln Asn Leu Leu
            625                 630                 635 caa gca gct ggg aac gtg ggc cag gcc agt ggg gag ctg ttg caa caa         2088
Gln Ala Ala Gly Asn Val Gly Gln Ala Ser Gly Glu Leu Leu Gln Gln
            640                 645                 650 att ggg gaa agt gat act gac ccc cac ttc cag gat gcg cta atg cag         2136
Ile Gly Glu Ser Asp Thr Asp Pro His Phe Gln Asp Ala Leu Met Gln
655                 660                 665                 670 ctc gcc aaa gct gtg gca agt gct gca gct gcc ctg gtc ctc aag gcc         2184
Leu Ala Lys Ala Val Ala Ser Ala Ala Ala Leu Val Leu Lys Ala
                675                 680                 685 aag agt gtg gcc cag cgg aca gag gac tcg gga ctt cag acc caa gtt         2232
Lys Ser Val Ala Gln Arg Thr Glu Asp Ser Gly Leu Gln Thr Gln Val
            690                 695                 700 att gct gca gca aca cag tgt gcc cta tcc act tcc caa cta gtg gcc         2280
Ile Ala Ala Ala Thr Gln Cys Ala Leu Ser Thr Ser Gln Leu Val Ala
705                 710                 715 tgt act aag gtg gtg gca cct aca atc agc tca cct gtc tgc caa gag         2328
Cys Thr Lys Val Val Ala Pro Thr Ile Ser Ser Pro Val Cys Gln Glu
            720                 725                 730 caa ctg gtg gag gct gga cga ctg gta gcc aaa gcc gtg gag ggc tgt         2376
Gln Leu Val Glu Ala Gly Arg Leu Val Ala Lys Ala Val Glu Gly Cys
735                 740                 745                 750 gtg tct gcc tcc cag gca gct aca gag gat ggg caa ctg ttg cga ggg         2424
Val Ser Ala Ser Gln Ala Ala Thr Glu Asp Gly Gln Leu Leu Arg Gly
                755                 760                 765 gta gga gca gca gcc aca gct gtc acc cag gcc cta aat gag ctg ctg         2472
Val Gly Ala Ala Ala Thr Ala Val Thr Gln Ala Leu Asn Glu Leu Leu

|  |  |
|---|---|
| cag cat gtg aaa gcc cat gcc aca ggg gct ggg cct gct ggc cgt tat<br>Gln His Val Lys Ala His Ala Thr Gly Ala Gly Pro Ala Gly Arg Tyr<br>           785                       790                       795 | 2520 |
| gac cag gct act gac acc atc cta acc gtc act gag aac atc ttt agc<br>Asp Gln Ala Thr Asp Thr Ile Leu Thr Val Thr Glu Asn Ile Phe Ser<br>800                        805                       810 | 2568 |
| tcc atg ggt gat gct ggg gag atg gtg gga cag gcc cgc atc ctg gcc<br>Ser Met Gly Asp Ala Gly Glu Met Val Gly Gln Ala Arg Ile Leu Ala<br>815                        820                       825              830 | 2616 |
| caa gcc aca tct gac ctg gtc aat gcc atc aag gct gat gct gag ggg<br>Gln Ala Thr Ser Asp Leu Val Asn Ala Ile Lys Ala Asp Ala Glu Gly<br>           835                       840                       845 | 2664 |
| gaa agt gat ctg gag aac tcc cgc aag ctc tta agt gct gcc aag atc<br>Glu Ser Asp Leu Glu Asn Ser Arg Lys Leu Leu Ser Ala Ala Lys Ile<br>           850                       855                       860 | 2712 |
| cta gct gat gcc aca gcc aag atg gta gag gct gcc aag gga gca gct<br>Leu Ala Asp Ala Thr Ala Lys Met Val Glu Ala Ala Lys Gly Ala Ala<br>           865                       870                       875 | 2760 |
| gcc cac cct gac agt gag gag cag cag cag cgg ctg cgg gag gca gct<br>Ala His Pro Asp Ser Glu Glu Gln Gln Gln Arg Leu Arg Glu Ala Ala<br>           880                       885                       890 | 2808 |
| gag ggg ctg cgc atg gcc acc aat gca gct gcg cag aat gcc atc aag<br>Glu Gly Leu Arg Met Ala Thr Asn Ala Ala Ala Gln Asn Ala Ile Lys<br>895                        900                       905              910 | 2856 |
| aaa aag ctg gtg cag cgc ctg gag cat gca gcc aag cag gct gca gcc<br>Lys Lys Leu Val Gln Arg Leu Glu His Ala Ala Lys Gln Ala Ala Ala<br>           915                       920                       925 | 2904 |
| tca gcc aca cag acc atc gct gca gct cag cac gca gcc tct acc ccc<br>Ser Ala Thr Gln Thr Ile Ala Ala Gln His Ala Ala Ser Thr Pro<br>           930                       935                       940 | 2952 |
| aaa gcc tct gcc ggc ccc cag ccc ctg ctg gtg cag agc tgc aag gca<br>Lys Ala Ser Ala Gly Pro Gln Pro Leu Leu Val Gln Ser Cys Lys Ala<br>           945                       950                       955 | 3000 |
| gtg gca gag cag att cca ctg ctg gtg cag ggc gtc cga gga agc caa<br>Val Ala Glu Gln Ile Pro Leu Leu Val Gln Gly Val Arg Gly Ser Gln<br>           960                       965                       970 | 3048 |
| gcc cag cct gac agc ccc agc gct cag ctt gcc ctc att gct gcc agc<br>Ala Gln Pro Asp Ser Pro Ser Ala Gln Leu Ala Leu Ile Ala Ala Ser<br>975                        980                       985              990 | 3096 |
| cag agc ttc ctg cag cca ggt ggg aag atg gtg gca gct gca aag gcc<br>Gln Ser Phe Leu Gln Pro Gly Gly Lys Met Val Ala Ala Lys Ala<br>           995                       1000                   1005 | 3144 |
| tca gtg cca acg att cag gac cag gct tca gcc atg cag ctg agt cag<br>Ser Val Pro Thr Ile Gln Asp Gln Ala Ser Ala Met Gln Leu Ser Gln<br>           1010                      1015                   1020 | 3192 |
| tgt gcc aag aac ctg ggc acc gcg ctg gct gaa ctc cgg acg gct gcc<br>Cys Ala Lys Asn Leu Gly Thr Ala Leu Ala Glu Leu Arg Thr Ala Ala<br>           1025                      1030                   1035 | 3240 |
| cag aag gct cag gaa gca tgt gga cct ttg gag atg gat tct gca ctg<br>Gln Lys Ala Gln Glu Ala Cys Gly Pro Leu Glu Met Asp Ser Ala Leu<br>1040                         1045                      1050 | 3288 |
| agt gtg gta cag aat cta gag aaa gat cta cag gaa gtg aag gca gca<br>Ser Val Val Gln Asn Leu Glu Lys Asp Leu Gln Glu Val Lys Ala Ala<br>1055                         1060                      1065                   1070 | 3336 |
| gct cga gat ggc aag ctt aaa ccc tta cct ggg gag aca atg gag aag<br>Ala Arg Asp Gly Lys Leu Lys Pro Leu Pro Gly Glu Thr Met Glu Lys<br>           1075                      1080                   1085 | 3384 |
| tgt acc cag gac ctg ggc aac agc acc aaa gcc gtg agc tca gcc atc | 3432 |

```
              Cys Thr Gln Asp Leu Gly Asn Ser Thr Lys Ala Val Ser Ser Ala Ile
                          1090                1095                1100 gcc cag cta ctg gga gag gtt gcc cag ggc aat gag aat tat gca ggt          3480
Ala Gln Leu Leu Gly Glu Val Ala Gln Gly Asn Glu Asn Tyr Ala Gly
            1105                1110                1115 att gca gct cgg gat gtg gca ggt ggg ctg cgg tca ctg gcc cag gcc          3528
Ile Ala Ala Arg Asp Val Ala Gly Gly Leu Arg Ser Leu Ala Gln Ala
        1120                1125                1130 gct agg gga gtc gct gca ctg acg tca gat cct gca gtg cag gcc att          3576
Ala Arg Gly Val Ala Ala Leu Thr Ser Asp Pro Ala Val Gln Ala Ile
1135                1140                1145                1150 gta ctt gat acg gcc agt gat gtg ctg gac aag gcc agc agc ctc att          3624
Val Leu Asp Thr Ala Ser Asp Val Leu Asp Lys Ala Ser Ser Leu Ile
                1155                1160                1165 gag gag gcg aaa aag gca gct ggc cat cca ggg gac cct gag agc cag          3672
Glu Glu Ala Lys Lys Ala Ala Gly His Pro Gly Asp Pro Glu Ser Gln
            1170                1175                1180 cag cgg ctt gcc cag gtg gct aaa gca gtg acc cag gct ctg aac cgc          3720
Gln Arg Leu Ala Gln Val Ala Lys Ala Val Thr Gln Ala Leu Asn Arg
        1185                1190                1195 tgt gtc agc tgc cta cct ggc cag cgc gat gtg gat aat gcc ctg agg          3768
Cys Val Ser Cys Leu Pro Gly Gln Arg Asp Val Asp Asn Ala Leu Arg
    1200                1205                1210 gca gtt gga gat gcc agc aag cga ctc ctg agt gac ttg ctt cct cct          3816
Ala Val Gly Asp Ala Ser Lys Arg Leu Leu Ser Asp Leu Leu Pro Pro
1215                1220                1225                1230 agc act ggg aca ttt caa gaa gct cag agc cgg ttg aat gaa gct gct          3864
Ser Thr Gly Thr Phe Gln Glu Ala Gln Ser Arg Leu Asn Glu Ala Ala
                1235                1240                1245 gct ggg ctg aat cag gca gcc aca gaa ctg gtg cag gcc tct cgg gga          3912
Ala Gly Leu Asn Gln Ala Ala Thr Glu Leu Val Gln Ala Ser Arg Gly
            1250                1255                1260 acc cct cag gac ctg gct cga gcc tca ggc cga ttt gga cag gac ttc          3960
Thr Pro Gln Asp Leu Ala Arg Ala Ser Gly Arg Phe Gly Gln Asp Phe
        1265                1270                1275 agc acc ttc ctg gaa gct ggt gtg gag atg gca ggc cag gct ccg agc          4008
Ser Thr Phe Leu Glu Ala Gly Val Glu Met Ala Gly Gln Ala Pro Ser
    1280                1285                1290 cag gag gac cga gcc caa gtt gtg tcc aac ttg aag ggc atc tcc atg          4056
Gln Glu Asp Arg Ala Gln Val Val Ser Asn Leu Lys Gly Ile Ser Met
1295                1300                1305                1310 tcc tca agc aaa ctt ctt ctg gct gcc aag gcc ctg tcc acg gac cct          4104
Ser Ser Ser Lys Leu Leu Leu Ala Ala Lys Ala Leu Ser Thr Asp Pro
                1315                1320                1325 gct gcc cct aac ctc aag agt cag ctg gct gca gct gcc agg gca gta          4152
Ala Ala Pro Asn Leu Lys Ser Gln Leu Ala Ala Ala Arg Ala Val
            1330                1335                1340 act gac agc atc aat cag ctc atc act atg tgc acc cag cag gca ccc          4200
Thr Asp Ser Ile Asn Gln Leu Ile Thr Met Cys Thr Gln Gln Ala Pro
        1345                1350                1355 ggc cag aag gag tgt gat aac gcc ctg cgg gaa ttg gag acg gtc cgg          4248
Gly Gln Lys Glu Cys Asp Asn Ala Leu Arg Glu Leu Glu Thr Val Arg
    1360                1365                1370 gaa ctc ctg gag aac cca gtc cag ccc atc aat gac atg tcc tac ttt          4296
Glu Leu Leu Glu Asn Pro Val Gln Pro Ile Asn Asp Met Ser Tyr Phe
1375                1380                1385                1390 ggt tgc ctg gac agt gta atg gag aac tca aag gtg ctg ggc gag gcc          4344
Gly Cys Leu Asp Ser Val Met Glu Asn Ser Lys Val Leu Gly Glu Ala
                1395                1400                1405
```

```
atg act ggc atc tcc caa aat gcc aag aac gga aac ctg cca gag ttt       4392
Met Thr Gly Ile Ser Gln Asn Ala Lys Asn Gly Asn Leu Pro Glu Phe
        1410                1415                1420 gga gat gcc att tcc aca gcc tca aag gca ctt tgt ggc ttc acc gag       4440
Gly Asp Ala Ile Ser Thr Ala Ser Lys Ala Leu Cys Gly Phe Thr Glu
    1425                1430                1435 gca gct gca cag gct gca tat ctg gtt ggt gtc tct gac ccc aat agc       4488
Ala Ala Ala Gln Ala Ala Tyr Leu Val Gly Val Ser Asp Pro Asn Ser
1440                1445                1450 caa gct gga cag caa ggg cta gtg gag ccc aca cag ttt gcc cgt gca       4536
Gln Ala Gly Gln Gln Gly Leu Val Glu Pro Thr Gln Phe Ala Arg Ala
 1455                1460                1465                1470 aac cag gca att cag atg gcc tgc cag agt ttg gga gag cct ggc tgt       4584
Asn Gln Ala Ile Gln Met Ala Cys Gln Ser Leu Gly Glu Pro Gly Cys
                1475                1480                1485 acc cag gcc cag gtg ctc tct gca gcc acc att gtg gct aaa cac acc       4632
Thr Gln Ala Gln Val Leu Ser Ala Ala Thr Ile Val Ala Lys His Thr
            1490                1495                1500 tct gca ctg tgt aac agc tgt cgc ctg gct tct gcc cgt acc acc aat       4680
Ser Ala Leu Cys Asn Ser Cys Arg Leu Ala Ser Ala Arg Thr Thr Asn
        1505                1510                1515 cct act gcc aag cgc cag ttt gta cag tca gcc aag gag gtg gcc aac       4728
Pro Thr Ala Lys Arg Gln Phe Val Gln Ser Ala Lys Glu Val Ala Asn
    1520                1525                1530 agc aca gct aat ctt gtc aag acc atc aag gcg cta gat ggg cct ttc       4776
Ser Thr Ala Asn Leu Val Lys Thr Ile Lys Ala Leu Asp Gly Pro Phe
1535                1540                1545                1550 aca gag gag aac cgt gcc cag tgc cga gca gca aca gcc cct ctg ctg       4824
Thr Glu Glu Asn Arg Ala Gln Cys Arg Ala Ala Thr Ala Pro Leu Leu
                1555                1560                1565 gag gct gtg gac aat ctg agt gcc ttt gcg tcc aac cct gag ttc tcc       4872
Glu Ala Val Asp Asn Leu Ser Ala Phe Ala Ser Asn Pro Glu Phe Ser
            1570                1575                1580 agc att cct gcc cag atc agc cct gag ggt cgg gct gcc atg gag ccc       4920
Ser Ile Pro Ala Gln Ile Ser Pro Glu Gly Arg Ala Ala Met Glu Pro
        1585                1590                1595 att gtg atc tct gcc cag aca atg tta gag agt gcc ggg gga ctc atc       4968
Ile Val Ile Ser Ala Gln Thr Met Leu Glu Ser Ala Gly Gly Leu Ile
    1600                1605                1610 cag aca gcc cgg gcc ctc gca gtc aac ccc cgg gac ccc ccg agc tgg       5016
Gln Thr Ala Arg Ala Leu Ala Val Asn Pro Arg Asp Pro Pro Ser Trp
1615                1620                1625                1630 tcg gtg ctg gcc ggc cac tcc cgt act gtc tca gac tcc atc aag aag       5064
Ser Val Leu Ala Gly His Ser Arg Thr Val Ser Asp Ser Ile Lys Lys
                1635                1640                1645 cta att aca agc atg agg gac aag gct cca ggg cag ctg gag tgt gaa       5112
Leu Ile Thr Ser Met Arg Asp Lys Ala Pro Gly Gln Leu Glu Cys Glu
            1650                1655                1660 acg gcc att gca gct ctg aac agt tgt cta cgg gac cta gac cag gct       5160
Thr Ala Ile Ala Ala Leu Asn Ser Cys Leu Arg Asp Leu Asp Gln Ala
        1665                1670                1675 tcc ctc gct gca gtc agc cag cag ctt gct ccc cgt gag gga atc tct       5208
Ser Leu Ala Ala Val Ser Gln Gln Leu Ala Pro Arg Glu Gly Ile Ser
    1680                1685                1690 caa gag gcc ttg cac act gag atg ctg act gca gtc caa gag atc tcc       5256
Gln Glu Ala Leu His Thr Glu Met Leu Thr Ala Val Gln Glu Ile Ser
1695                1700                1705                1710 cat ctc att gag ccg ctg gcc cat gct gcc cgg gct gaa gcc tcc cag       5304
His Leu Ile Glu Pro Leu Ala His Ala Ala Arg Ala Glu Ala Ser Gln
                1715                1720                1725
```

```
ctg gga cac aag gtg tcc cag atg gcg cag tac ttt gag ccg ctc acc         5352
Leu Gly His Lys Val Ser Gln Met Ala Gln Tyr Phe Glu Pro Leu Thr
            1730                1735                1740 ctg gct gca gtg ggt gct gcc tcc aag acc ctg agc cac ccg cag cag         5400
Leu Ala Ala Val Gly Ala Ala Ser Lys Thr Leu Ser His Pro Gln Gln
        1745                1750                1755 atg gca ctc ctg gac cag act aaa aca ttg gca gag tct gcc ctg cag         5448
Met Ala Leu Leu Asp Gln Thr Lys Thr Leu Ala Glu Ser Ala Leu Gln
    1760                1765                1770 ttg cta tac act gcc aag gag gct ggt ggt aac cca aag caa gca gct         5496
Leu Leu Tyr Thr Ala Lys Glu Ala Gly Gly Asn Pro Lys Gln Ala Ala
1775                1780                1785                1790 cac acc cag gaa gcc ctg gag gag gct gtg cag atg atg acc gag gcc         5544
His Thr Gln Glu Ala Leu Glu Glu Ala Val Gln Met Met Thr Glu Ala
                1795                1800                1805 gta gag gac ctg aca aca acc ctc aac gag gca gcc agt gct gct ggg         5592
Val Glu Asp Leu Thr Thr Thr Leu Asn Glu Ala Ala Ser Ala Ala Gly
            1810                1815                1820 gtc gtg ggt ggc atg gtg gac tcc atc acc cag gcc atc aac cag cta         5640
Val Val Gly Gly Met Val Asp Ser Ile Thr Gln Ala Ile Asn Gln Leu
        1825                1830                1835 gat gaa gga cca atg ggt gaa cca gaa ggt tcc ttc gtg gat tac caa         5688
Asp Glu Gly Pro Met Gly Glu Pro Glu Gly Ser Phe Val Asp Tyr Gln
    1840                1845                1850 aca act atg gtg cgg aca gcc aag gcc att gca gtg act gtt cag gag         5736
Thr Thr Met Val Arg Thr Ala Lys Ala Ile Ala Val Thr Val Gln Glu
1855                1860                1865                1870 atg gtt acc aag tca aac acc agc cca gag gag ctg ggc cct ctt gct         5784
Met Val Thr Lys Ser Asn Thr Ser Pro Glu Glu Leu Gly Pro Leu Ala
                1875                1880                1885 aac cag ctg acc agt gac tat ggc cgt ctg gcc tcg gag gcc aag cct         5832
Asn Gln Leu Thr Ser Asp Tyr Gly Arg Leu Ala Ser Glu Ala Lys Pro
            1890                1895                1900 gca gcg gtg gct gct gaa aat gaa gag ata ggt tcc cat atc aaa cac         5880
Ala Ala Val Ala Ala Glu Asn Glu Glu Ile Gly Ser His Ile Lys His
        1905                1910                1915 cgg gta cag gag ctg ggc cat ggc tgt gcc gct ctg gtc acc aag gca         5928
Arg Val Gln Glu Leu Gly His Gly Cys Ala Ala Leu Val Thr Lys Ala
    1920                1925                1930 ggc gcc ctg cag tgc agc ccc agt gat gcc tac acc aag aag gag ctc         5976
Gly Ala Leu Gln Cys Ser Pro Ser Asp Ala Tyr Thr Lys Lys Glu Leu
1935                1940                1945                1950 ata gag tgt gcc cgg aga gtc tct gag aag gtc tcc cac gtc ctg cgt         6024
Ile Glu Cys Ala Arg Arg Val Ser Glu Lys Val Ser His Val Leu Arg
                1955                1960                1965 gcg ctc cag gct ggg aat cgt ggc acc cag gcc tgc atc aca gca gcc         6072
Ala Leu Gln Ala Gly Asn Arg Gly Thr Gln Ala Cys Ile Thr Ala Ala
            1970                1975                1980 agc gct gtg tct ggt att att gct gac ctc gac acc acc atc atg ttc         6120
Ser Ala Val Ser Gly Ile Ile Ala Asp Leu Asp Thr Thr Ile Met Phe
        1985                1990                1995 gcc act gct ggc acg ctc aat cgt gag ggt act gaa act ttc gct gac         6168
Ala Thr Ala Gly Thr Leu Asn Arg Glu Gly Thr Glu Thr Phe Ala Asp
    2000                2005                2010 cac cgg gag ggc atc ctg aag act gcg aag gtg ctg gtg gag gac acc         6216
His Arg Glu Gly Ile Leu Lys Thr Ala Lys Val Leu Val Glu Asp Thr
2015                2020                2025                2030 aag gtc ctg gtg caa aac gca gct ggg agc cag gag aag ttg gcg cag         6264
Lys Val Leu Val Gln Asn Ala Ala Gly Ser Gln Glu Lys Leu Ala Gln
```

-continued

```
                 2035                  2040                  2045
gct gcc cag tcc tcc gtg gcg acc atc acc cgc ctc gct gat gtg gtc      6312
Ala Ala Gln Ser Ser Val Ala Thr Ile Thr Arg Leu Ala Asp Val Val
            2050                  2055                  2060 aag ctg ggt gca gcc agc ctg gga gct gag gac cct gag acc cag gtg      6360
Lys Leu Gly Ala Ala Ser Leu Gly Ala Glu Asp Pro Glu Thr Gln Val
        2065                  2070                  2075 gta cta atc aac gca gtg aaa gat gta gcc aaa gcc ctg gga gac ctc      6408
Val Leu Ile Asn Ala Val Lys Asp Val Ala Lys Ala Leu Gly Asp Leu
    2080                  2085                  2090 atc agt gca acg aag gct gca gct ggc aaa gtt gga gat gac cct gct      6456
Ile Ser Ala Thr Lys Ala Ala Ala Gly Lys Val Gly Asp Asp Pro Ala
2095                  2100                  2105                  2110 gtg tgg cag cta aag aac tct gcc aag gtg atg gtg acc aat gtg aca      6504
Val Trp Gln Leu Lys Asn Ser Ala Lys Val Met Val Thr Asn Val Thr
                2115                  2120                  2125 tca ttg ctt aag aca gta aaa gcc gtg gaa gat gag gcc acc aaa ggc      6552
Ser Leu Leu Lys Thr Val Lys Ala Val Glu Asp Glu Ala Thr Lys Gly
            2130                  2135                  2140 act cgg gcc ctg gag gca acc aca gaa cac ata cgg cag gag ctg gcg      6600
Thr Arg Ala Leu Glu Ala Thr Thr Glu His Ile Arg Gln Glu Leu Ala
        2145                  2150                  2155 gtt ttc tgt tcc cca gag cca cct gcc aag acc tct acc cca gaa gac      6648
Val Phe Cys Ser Pro Glu Pro Pro Ala Lys Thr Ser Thr Pro Glu Asp
    2160                  2165                  2170 ttc atc cga atg acc aag ggt atc acc atg gca acc gcc aag gcc gtt      6696
Phe Ile Arg Met Thr Lys Gly Ile Thr Met Ala Thr Ala Lys Ala Val
2175                  2180                  2185                  2190 gct gct ggc aat tcc tgt cgc cag gaa gat gtc att gcc aca gcc aat      6744
Ala Ala Gly Asn Ser Cys Arg Gln Glu Asp Val Ile Ala Thr Ala Asn
                2195                  2200                  2205 ctg agc cgc cgt gct att gca gat atg ctt cgg gct tgc aag gaa gca      6792
Leu Ser Arg Arg Ala Ile Ala Asp Met Leu Arg Ala Cys Lys Glu Ala
            2210                  2215                  2220 gct tac cac cca gaa gtg gcc cct gat gtg cgg ctt cga gcc ctg cac      6840
Ala Tyr His Pro Glu Val Ala Pro Asp Val Arg Leu Arg Ala Leu His
        2225                  2230                  2235 tat ggc cgg gag tgt gcc aat ggc tac ctg gaa ctg ctg gac cat gta      6888
Tyr Gly Arg Glu Cys Ala Asn Gly Tyr Leu Glu Leu Leu Asp His Val
    2240                  2245                  2250 ctg ctg acc ctg cag aag cca agc cca gaa ctc aag cag cag ttg aca      6936
Leu Leu Thr Leu Gln Lys Pro Ser Pro Glu Leu Lys Gln Gln Leu Thr
2255                  2260                  2265                  2270 gga cat tca aag cgt gtg gct ggt tcc gtc act gag ctc atc cag gct      6984
Gly His Ser Lys Arg Val Ala Gly Ser Val Thr Glu Leu Ile Gln Ala
                2275                  2280                  2285 gct gaa gcc atg aag gga aca gaa tgg gta gac cca gag gac ccc aca      7032
Ala Glu Ala Met Lys Gly Thr Glu Trp Val Asp Pro Glu Asp Pro Thr
            2290                  2295                  2300 gtc att gct gag aat gag ctc ctg gga gct gca gcc gcc att gag gct      7080
Val Ile Ala Glu Asn Glu Leu Leu Gly Ala Ala Ala Ala Ile Glu Ala
        2305                  2310                  2315 gca gcc aaa aag cta gag cag ctg aag ccc cgg gcc aaa ccc aag gag      7128
Ala Ala Lys Lys Leu Glu Gln Leu Lys Pro Arg Ala Lys Pro Lys Glu
    2320                  2325                  2330 gca gat gag tcc ttg aac ttt gag gag cag ata cta gaa gct gcc aag      7176
Ala Asp Glu Ser Leu Asn Phe Glu Glu Gln Ile Leu Glu Ala Ala Lys
2335                  2340                  2345                  2350 tcc att gca gca gcc acc agt gca ctg gta aag gct gcg tcg gct gcc      7224
```

-continued

```
Ser Ile Ala Ala Ala Thr Ser Ala Leu Val Lys Ala Ala Ser Ala Ala
             2355                2360                2365 cag aga gaa cta gtg gcc caa ggg aag gtg ggt gcc att cca gcc aat    7272
Gln Arg Glu Leu Val Ala Gln Gly Lys Val Gly Ala Ile Pro Ala Asn
             2370                2375                2380 gca ctg gac gat ggg cag tgg tcc cag ggc ctc att tct gct gcc cgg    7320
Ala Leu Asp Asp Gly Gln Trp Ser Gln Gly Leu Ile Ser Ala Ala Arg
             2385                2390                2395 atg gtg gct gcg gcc acc aac aat ctg tgt gag gca gcc aat gca gct    7368
Met Val Ala Ala Ala Thr Asn Asn Leu Cys Glu Ala Ala Asn Ala Ala
     2400                2405                2410 gta caa ggc cat gcc agc cag gag aag ctc atc tca tca gcc aag cag    7416
Val Gln Gly His Ala Ser Gln Glu Lys Leu Ile Ser Ser Ala Lys Gln
2415                2420                2425                2430 gta gct gcc tcc aca gcc cag ctc ctt gtg gcc tgc aag gtc aag gct    7464
Val Ala Ala Ser Thr Ala Gln Leu Leu Val Ala Cys Lys Val Lys Ala
             2435                2440                2445 gac cag gac tcg gag gca atg aaa cga ctt cag gct gct ggc aac gca    7512
Asp Gln Asp Ser Glu Ala Met Lys Arg Leu Gln Ala Ala Gly Asn Ala
             2450                2455                2460 gtg aag cga gcc tca gat aat ctg gtg aaa gca gca cag aag gct gca    7560
Val Lys Arg Ala Ser Asp Asn Leu Val Lys Ala Ala Gln Lys Ala Ala
             2465                2470                2475 gcc ttt gaa gag cag gag aat gag aca gtg gtg gtg aaa gag aag atg    7608
Ala Phe Glu Glu Gln Glu Asn Glu Thr Val Val Val Lys Glu Lys Met
             2480                2485                2490 gtt ggc ggc att gcc cag atc atc gca gca cag gaa gaa atg ctt cgg    7656
Val Gly Gly Ile Ala Gln Ile Ile Ala Ala Gln Glu Glu Met Leu Arg
2495                2500                2505                2510 aag gaa cga gag ctg gaa gag gcg cgg aag aaa ctg gcc cag atc cgg    7704
Lys Glu Arg Glu Leu Glu Glu Ala Arg Lys Lys Leu Ala Gln Ile Arg
             2515                2520                2525 cag cag cag tac aag ttt ctg cct tca gag ctt cga gat gag cac taa    7752
Gln Gln Gln Tyr Lys Phe Leu Pro Ser Glu Leu Arg Asp Glu His
             2530                2535                2540 agaagcctct tctatttaat gcagacccgg cccagagact gtgcgtgcca ctaccaaagc    7812
cttctgggct gtcggggccc aacctgccca accccagcac tccccaaagt gcctgccaaa    7872 ccccagggc tggccccgcc cagtcccgca gtacatcccc tgtcccctcc caacccaa       7932 gtgccttcat gccctagggc cccccaagtg cctgcccctc ccagagtat taactctcca    7992 agagtattat taacgctgct gtacctcgat ctgaatctgc cggggcccca gcccactcca    8052
ccctgccagc acttccagcc agtccc                                         8078
```

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
cgatgcagtt tgagccgtct a     21

<210> SEQ ID NO 5
<211> LENGTH: 24
<212> TYPE: DNA
<213> ORGANISM: Artificial Sequence
<220> FEATURE:
<223> OTHER INFORMATION: PCR Primer -continued

<400> SEQUENCE: 5
atctgacaga aagagcccaa agtc                                              24

<210> SEQ ID NO 6
<211> LENGTH: 21
<212> TYPE: DNA
<213> ORGANISM: Artificial Sequence
<220> FEATURE:
<223> OTHER INFORMATION: PCR Probe

<400> SEQUENCE: 6
acgcctgccg catcattcgt g                                                 21

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                    19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                   20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                   20

<210> SEQ ID NO 10
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 10
ctccttcgtc ttggtatatt                                                   20

<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 11
tgcgctgcct ggctctcgcc                                                   20

<210> SEQ ID NO 12
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 12
gcaaccatgg tggcagcttc                                              20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
atcgtcttca ccacattccc                                              20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
tgcggcaggc gtcgtacacc                                              20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
aaagagccca aagtcgctgg                                              20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
gtagtagtcc aaagctttcc                                              20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
tgtttcttcc tgtactccat                                              20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
```
gtcatccacc atgatcgtct                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
cgggcacaga tggtcatgag                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ctctcgaacc aatgaatatt                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
ttcatctcgc agcaatgtct                                              20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
atggtccagc cagttcaact                                              20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
tgagtaaaag aacttcctgc                                              20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ctcgtgcctg cacatacagg                                              20

<210> SEQ ID NO 25
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 25
agcaaactca caggccttgt                                                20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
aaggaagcca gccttgtgct                                                20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
atcttacgct ctcccttctg                                                20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
gcggaccttg gcctcaatct                                                20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
tccttcacca ggaagaagga                                                20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
actcgcatca cacactcctt                                                20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gcgtttgatg ttggtgaggt                                                20
```

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
agccatcttg gtaatctcca                                         20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
gcaatgagct gtgcaatctg                                         20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
catctccttc cagcccaaag                                         20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
ccggttgtat tgctgctgca                                         20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ccagaggctc cagagcgcat                                         20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
tgcatctggc cgctggtaat                                         20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tggttccagt gagtgcctgc                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
aagtcatcca gggtggcctg                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
tttgattcat ccatcttgtt                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
caccacagac gcagtaccag                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
cagcccactg cggtatagtc                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
agcttcaccc cacgggacat                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ccctttgctg cctgcaacag                                              20

<210> SEQ ID NO 45

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
actggctggt tgggcactgc                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ccaatttgtt gcaacagctc                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gctgcagcac ttgccacagc                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
gtcccgagtc ctctgtccgc                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
cactagttgg gaagtggata                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
agttgctctt ggcagacagg                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
```
cctgggaggc agacacacag                                    20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
tcatttaggg cctgggtgac                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tcagtagcct ggtcataacg                                    20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ggcctgtccc accatctccc                                    20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
tcagcatcag ccttgatggc                                    20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
tggctgtggc atcagctagg                                    20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
tgctgctgct cctcactgtc                                    20

<210> SEQ ID NO 58
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 58
tggcattctg cgcagctgca                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
agcgatggtc tgtgtggctg                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ggacgccctg caccagcagt                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ccaccatctt cccacctggc                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
cggtgcccag gttcttggca                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
cactcagtgc agaatccatc                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
gggtacactt ctccattgtc                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cctgggcaac ctctcccagt                                            20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
ccctagcggc ctgggccagt                                            20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
ggccttgtcc agcacatcac                                            20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ctgacacagc ggttcagagc                                            20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
agtcactcag gagtcgcttg                                            20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gctgcctgat tcagcccagc                                            20

<210> SEQ ID NO 71
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 71
gaaggtgctg aagtcctgtc                                               20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
gagatgccct tcaagttgga                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
cagttactgc cctggcagct                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tccaattccc gcagggcgtt                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gttctccatt acactgtcca                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ggcatctcca aactctggca                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
caaactctgg caggccatct                                               20
```

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
tacaaactgg cgcttggcag                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ggttggacgc aaaggcactc                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
tgtccctcat gcttgtaatt                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
cagcatctca gtgtgcaagg                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
tccaccagca ccttcgcagt                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
cagcaacggc cttggcggtt                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide -continued

```
<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
tgtctcattc tcctgctctt                                                    20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
gaggcttctt tagtgctcat                                                    20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ctgcattaaa tagaagaggc                                                    20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
ttggtagtgg cacgcacagt                                                    20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
cagattcaga tcgaggtaca                                                    20
```

ANTISENSE MODULATION OF TALIN EXPRESSION

FIELD OF THE INVENTION

The present invention provides compositions and methods for modulating the expression of Talin. In particular, this invention relates to antisense compounds, particularly oligonucleotides, specifically hybridizable with nucleic acids encoding human Talin. Such oligonucleotides have been shown to modulate the expression of Talin.

BACKGROUND OF THE INVENTION

Cell adhesive contacts are critical for the development and maintenance of multicellular organisms. These contacts are mediated by cell adhesion molecules (CAMs), a versatile class of compounds expressed on the cell surface. Cells adhere to one another and to extracellular substrates through the concerted action of a variety of CAMs, which act as both receptors and ligands on opposing cells.

These contacts are also critical for the bidirectional transduction of signals to the interior of the cell and, consequently, to the modulation of biochemical pathways. Integrins, one group of transmembrane CAMs, are heterodimeric cation-dependent glycoproteins and have been found in all tissues examined. They are comprised of a large extracellular domain, a transmembrane domain and a smaller cytoplasmic domain. It is the extracellular domain of the integrin that acts as a receptor for various matrix proteins, while the cytoplasmic domain has been shown to interact with actin filaments of the cytoskeleton and with cytoplasmic proteins such as talin, paxillin, filamin and focal adhesion kinase (FAK) (Critchley et al., Biochem. Soc. Symp., 1999, 65, 79–99).

Talin is a cytoplasmic protein that is concentrated at points of cell adhesion, membrane ruffles, the leading lamellae of the cell periphery and aligned with microfilament bundles, which acts to link cytoskeletal proteins to the integrins, thereby linking the extracellular matrix to other cells. Talin is a large dimeric protein and is post-translationally modified through phosphorylation by protein kinase C-delta (Litchfield and Ball, Biochem. Biophys. Res. Commun., 1986, 134, 1276–1283; Watters et al., Exp. Cell. Res., 1996, 229, 327–335) as well as by proteolytic cleavage events making it a central component of many signaling cascades.

Talin interacts with several cytoskeletal proteins including actin filaments, where it functions as a crosslinker, with these interactions being very sensitive to ionic strength, temperature and pH (Goldmann et al., Eur. J. Biochem., 1999, 260, 439–445; Schmidt et al., Arch. Biochem. Biophys., 1999, 366, 139–150; Zhang et al., Biochem. Biophys. Res. Commun., 1996, 218, 530–537). Talin also interacts with myosin (Lin et al., Biochem. Biophys. Res. Commun., 1998, 249, 656–659) and vinculin (Burridge and Mangeat, Nature, 1984, 308, 744–746; Goldmann et al., J. Muscle Res. Cell Motil., 1996, 17, 1–5), as well as the plasma membrane fibronectin receptor (Horwitz et al., Nature, 1986, 320, 531–533) and platelet integrins (Knezevic et al., J. Biol. Chem., 1996, 271, 16416–16421). Collectively, these studies strongly implicate talin in cell adhesion regulation and cell morphology. Interestingly, when the talin protein is added to liposomes in solution, holes form in the liposomes and become increasingly larger with increasing concentrations of added talin. This 'opening up' of the liposome continues until the liposome is transformed to a stable bilayer (Saitoh et al., Proc. Natl. Acad. Sci. U.S.A., 1998, 95, 1026–1031).

In tissues, talin has been localized to myotendinous junctions (sites of skeletal muscle adherence to tendons), where expression was shown to be regulated by mechanical loading (Frenette and Tidball, Am. J. Physiol., 1998, 275, C818–825; Tidball et al., J. Cell. Biol., 1986, 103, 1465–1472). Recently, it was further demonstrated that, in cardiomyocytes, talin participates in the transmission of contractile force to the extracellular matrix (Imanaka-Yoshida et al., Cell Motil. Cytoskeleton, 1999, 42, 1–11). These studies imply that the integrity and concentration of the talin protein could play a major role in determining muscle strength and cardiac function.

In prostate tissues, talin is highly expressed in epithelial cells, with lower levels in the stroma. The expression of talin in these cells is down-regulated by androgens, a phenomenon known to contribute to the development of prostate cancer (Betts et al., FEBS Lett., 1998, 434, 66–70).

Albiges-Rizo et al. have demonstrated that down-regulation of talin alters cell adhesion by slowing cell spreading of HeLa cells. In these studies, HeLa cells were transfected with a 5' region of the talin gene, in antisense orientation, under the control of an inducible promoter. It was shown that a reduction of talin expression impaired the folding and processing of integrins as well as reducing focal contacts (Albiges-Rizo et al., J. Cell. Sci., 1995, 108, 3317–3329).

Talin, originally called P235 in platelets, is an abundant protein in platelets and constitutes greater than 3% of the total protein (Beckerle et al., J. Cell. Biochem., 1986, 30, 259–270; Collier and Wang, FEBS Lett., 1982, 143, 205–210; Collier and Wang, J. Biol. Chem., 1982, 257, 6937–6943). The distribution of talin in resting and activated human platelets undergoes an activation-dependent change in its subcellular location. In resting platelets, which are nonadhesive, talin is uniformly distributed throughout the cytoplasm. In contrast, in activated platelets, talin is concentrated at the cytoplasmic face of the plasma membrane (Beckerle et al., J. Cell. Biol., 1989, 109, 3333–3346). The regulated redistribution of talin raises the possibility that talin plays a role in platelet adhesion (Beckerle and Yeh, Cell. Motil. Cytoskeleton, 1990, 16, 7–13).

Currently, there are no known therapeutic agents which effectively inhibit the synthesis of talin and strategies aimed at modulating talin expression and/or function have involved the use of antibodies and molecules that block protein kinase C activity. Priddle et al., *using gene replacement vectors, isolated mouse embryonic stem cells in which both copies of the talin gene were disrupted. These cells, when undifferentiated, were unable to spread, showed reduced adhesion and expressed low levels of beta integrin. However, upon differentiation, these cells demonstrate talin-independent wild-type characteristics (Priddle et al., J. Cell. Biol., 1998, 142, 1121–1133).*

Using monoclonal antibodies raised against the platelet form of talin, Bolton et al. have mapped the epitopes along the talin protein that are recognized by these antibodies and shown that microinjection of antibodies to two separate regions of talin inhibit cell motility (Bolton et al., Cell. Motil. Cytoskeleton, 1997, 36, 363–376). Implementing the same antibody strategy, others have shown that the talin dimer is comprised of two dumbbell-shaped antiparallel subunits (Isenberg and Goldmann, FEBS Lett., 1998, 426, 165–170).

However, because these strategies are untested as therapeutic protocols, there remains a long-felt need for additional agents capable of effectively inhibiting talin function.

Antisense technology is emerging as an effective means for reducing the expression of specific gene products and may therefore prove to be uniquely useful in a number of therapeutic, diagnostic, and research applications for the modulation of talin expression. The present invention provides compositions and methods for modulating talin expression using said antisense technology.

SUMMARY OF THE INVENTION

The present invention is directed to antisense compounds, particularly oligonucleotides, which are targeted to a nucleic acid encoding Talin, and which modulate the expression of Talin. Pharmaceutical and other compositions comprising the antisense compounds of the invention are also provided. Further provided are methods of modulating the expression of Talin in cells or tissues comprising contacting said cells or tissues with one or more of the antisense compounds or compositions of the invention. Further provided are methods of treating an animal, particularly a human, suspected of having or being prone to a disease or condition associated with expression of Talin by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding Talin, ultimately modulating the amount of Talin produced. This is accomplished by providing antisense compounds which specifically hybridize with one or more nucleic acids encoding Talin. As used herein, the terms "target nucleic acid" and "nucleic acid encoding Talin" encompass DNA encoding Talin, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Talin. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Talin. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Talin, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e. from about 8 to about 30 linked nucleosides). Particularly preferred antisense compounds are antisense oligonucleotides, even more preferably those comprising from about 12 to about 25 nucleobases. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be inked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$, also described in examples hereinbelow.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The*

*Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937).

Representative United States patents that teach the preparation of such oligonucleotide conjugates include, but are not limited to, U.S. Pat. Nos.: 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of Talin is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Talin, enabling sandwich and other assays to easily be constructed to exploit this fact. Hybridization of the antisense oligonucleotides of the invention with a nucleic acid encoding Talin can be detected by means known in the art. Such means may include conjugation of an enzyme to the oligonucleotide, radiolabelling of the oligonucleotide or any other suitable detection means. Kits using such detection means for detecting the level of Talin in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and triglycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms, Lieberman, Rieger and Banker (Eds.)*, 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S. T. P. *Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}215G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534, 899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 *In: Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., *PCT Application WO 97/30731*), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pages 1206–1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).
2'-Fluoro amidites
   2'-Fluorodeoxyadenosine amidites
   2'-fluoro oligonucleotides were synthesized as described previously [Kawasaki, et. al., *J. Med. Chem.*, 1993, 36, 831≧841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.
   2'-Fluorodeoxyguanosine
   The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.
   2'-Fluorouridine
   Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.
   2'-Fluorodeoxycytidine
   2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.
   2'-O-(2-Methoxyethyl)modified amidites
   2'-O-Methoxyethyl-substituted nucleoside amidites are prepared as follows, or alternatively, as per the methods of Martin, P., *Helvetica Chimica Acta*, 1995, 78, 486–504.
   2,2'-Anhydro[1-(beta-D-arabinofuranosyl)-5-methyluridine]
   5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.)
   2'-O-Methoxyethyl-5-methyluridine
   2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-methoxyethyl-5'-O-dimethoxytrityl-5-methylcytidine (74 g, 0.10 M) was dissolved in $CH_2Cl_2$ (1 L) Tetrazole diisopropylamine (7.1 g) and 2-cyanoethoxytetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl)nucleoside amidites and 2'-O-(dimethylaminooxyethyl)nucleoside amidites 2'-(Dimethylaminooxyethoxy)nucleoside amidites 2'-(Dimethylaminooxyethoxy)nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O²-2'-anhydro-5-methyluridine

O²-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O²-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.249, 44.36 mmol). It was then dried over P₂O₅ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry CH₂Cl₂ (4.5 mL) and methylhydrazine (300 mL, 4.64 mmol) was added dropwise at −10° C. to 0° C. After 1 h the mixture was filtered, the filtrate was washed with ice cold CH₂Cl₂ and the combined organic phase was washed with water, brine and dried over anhydrous Na₂SO₄. The solution was concentrated to get 2'-O-(aminooxyethyl)thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 9, 78%).

5'-O-tert-Butyldiphenylsilyl-2'-[N,N-dimethylaminooxyethyl]-5-methyluridine

5'-O-tert-butyldiphenylsilyl-2'-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in CH₂Cl₂). Aqueous NaHCO₃ solution (5%, 10 mL) was added and extracted with ethyl acetate (2×20 mL). Ethyl acetate phase was dried over anhydrous Na₂SO₄, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO₃ (25 mL) solution was added and extracted with ethyl acetate (2×25 mL). Ethyl acetate layer was dried over anhydrous Na₂SO₄ and evaporated to dryness. The residue obtained was purified by flash column chromatography and eluted with 5% MeOH in CH₂Cl₂ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH₂Cl₂). Solvent was removed under vacuum and the residue placed on a flash column and eluted with 10% MeOH in CH₂Cl₂ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P₂O₅ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy)nucleoside amidites

2'-(Aminooxyethoxy)nucleoside amidites [also known in the art as 2'-O-(aminooxyethyl)nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)]Chimeric Phosphorothioate Oligonucleotides

[2'-O-(2-methoxyethyl)]-[2'-deoxy]-[-2'-O-(methoxyethyl)]chimeric phosphorothioate oligonucleotides were prepared as per the procedure above for the 2'-O-methyl chimeric oligonucleotide, with the substitution of 2'-O-(methoxyethyl)amidites for the 2'-O-methyl amidites.

[2'-O-(2-Methoxyethyl)Phosphodiester]-[2'-deoxyphosphorothioate]-[2'-O-(2-Methoxyethyl) Phosphodiester]Chimeric Oligonucleotides

[2'-O-(2-methoxyethyl phosphodiester]-[2'-deoxyphosphorothioate]-[2'-O-(methoxyethyl) phosphodiester]chimeric oligonucleotides are prepared as per the above procedure for the 2'-O-methyl chimeric oligonucleotide with the substitution of 2'-O-(methoxyethyl) amidites for the 2'-O-methyl methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected betacyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following four cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human c-Ha-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized in subsequent experiments for that cell line. If 80% inhibition is not achieved, the lowest concentration of positive control oligonucleotide that results in 60% inhibition of c-Ha-ras or c-raf mRNA is then utilized in subsequent experiments for that cell line. If 60% inhibition is not achieved, that particular cell line is deemed as unsuitable for oligonucleotide transfection experiments.

Example 10

Analysis of Oligonucleotide Inhibition of Talin Expression

Antisense modulation of Talin expression can be assayed in a variety of ways known in the art. For example, Talin mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed as multiplexable. Other methods of PCR are also known in the art.

Talin protein levels can be quantitated in a variety of ways well known in the art, such as immunoprecipitation, Western blot analysis (immunoblotting), ELISA or fluorescence-activated cell sorting (FACS). Antibodies directed to Talin can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total mRNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Talin mRNA Levels

Quantitation of Talin mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either operon Technologies Inc., Alameda, Calif. or PE-Applied Biosystems, Foster City, Calif.) is attached to the 5' end of the probe and a quencher dye (e.g., TAMRA, obtained from either operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. RT-PCR reactions were carried out by adding 25 μL PCR cocktail (1× TAQMAN™ buffer A, 5.5 mM $MgCl_2$, 300 μM each of dATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL poly(A) mRNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension). Talin probes and primers were designed to hybridize to the human Talin sequence, using published sequence information (GenBank accession number AF078828, incorporated herein as SEQ ID NO:3).

For Talin the PCR primers were: forward primer: CGATGCAGTTTGAGCCGTCTA (SEQ ID NO: 4) reverse primer: ATCTGACAGAAAGAGCCCAAAGTC (SEQ ID NO: 5) and the PCR probe was: FAM-ACGCCTGCCGCATCATTCGTG-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye.

For GAPDH the PCR primers were: forward primer: GAAGGTGAAGGTCGGAGTC (SEQ ID NO: 7) reverse primer: GAAGATGGTGATGGGATTTC (SEQ ID NO: 8) and the PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Talin mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.).

Membranes were probed using QUICKHYB™ hybridization solution (Stratagene, La Jolla, Calif.) using manufacturer's recommendations for stringent conditions with a Talin specific probe prepared by PCR using the forward primer CGATGCAGTTTGAGCCGTCTA (SEQ ID NO: 4) and the reverse primer ATCTGACAGAAAGAGCCCAAAGTC (SEQ ID NO: 5). To normalize for variations in loading and transfer efficiency membranes were stripped and probed for glyceraldehyde-3-phosphate dehydrogenase (GAPDH) RNA (Clontech, Palo Alto, Calif.). Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Talin Expression-phosphorothioate 2'-MOE Gapmer Oligonucleotides In accordance with the present invention, a series of oligonucleotides targeted to human Talin were synthesized. The oligonucleotide sequences are shown in Table 1. Target sites are indicated by nucleotide numbers, as given in the sequence source reference (Genbank accession no. AF078828, incoorporated herein as SEQ ID NO: 3), to which the oligonucleotide binds.

All compounds in Table 1 are chimeric oligonucleotides ("gapers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines.

Data were obtained by real-time quantitative PCR as described in other examples herein and are averaged from two experiments. If present, "N.D." indicates "no data".

TABLE 1

Inhibition of Talin mRNA levels by chimeric phosphorothioate oligonucleotides having 2'-MOE wings and a deoxy gap

| ISIS# | REGION | TARGET SITE | SEQUENCE | Inhibition | SEQ ID NO. |
|---|---|---|---|---|---|
| 109109 | 5' UTR | 1 | ctccttcgtcttggtatatt | 0 | 10 |
| 109110 | 5' UTR | 73 | tgcgctgcctggctctcgcc | 73 | 11 |
| 109111 | Start Codon | 115 | gcaaccatggtggcagcttc | 94 | 12 |
| 109112 | Coding | 157 | atcgtcttcaccacattccc | 70 | 13 |
| 109113 | Coding | 198 | tgcggcaggcgtcgtacacc | 94 | 14 |
| 109114 | Coding | 257 | aaagagcccaaagtcgctgg | 93 | 15 |
| 109115 | Coding | 320 | gtagtagtccaaagcttttcc | 77 | 16 |
| 109116 | Coding | 361 | tgtttcttcctgtactccat | 88 | 17 |
| 109117 | Coding | 419 | gtcatccaccatgatcgtct | 68 | 18 |
| 109118 | Coding | 460 | cgggcacagatggtcatgag | 61 | 19 |
| 109119 | Coding | 503 | ctctcgaaccaatgaatatt | 43 | 20 |
| 109120 | Coding | 572 | ttcatctcgcagcaatgtct | 88 | 21 |
| 109121 | Coding | 635 | atggtccagccagttcaact | 81 | 22 |
| 109122 | Coding | 707 | tgagtaaaagaacttcctgc | 46 | 23 |
| 109123 | Coding | 768 | ctcgtgcctgcacatacagg | 89 | 24 |
| 109124 | Coding | 824 | agcaaactcacaggccttgt | 82 | 25 |
| 109125 | Coding | 887 | aaggaagccagccttgtgct | 79 | 26 |
| 109126 | Coding | 943 | atcttacgctctcccttctg | 57 | 27 |
| 109127 | Coding | 998 | gcggaccttggcctcaatct | 87 | 28 |
| 109128 | Coding | 1057 | tccttcaccaggaagaagga | 53 | 29 |
| 109129 | Coding | 1126 | actcgcatcacacactcctt | 70 | 30 |
| 109130 | Coding | 1181 | gcgtttgatgttggtgaggt | 66 | 31 |
| 109131 | Coding | 1236 | agccatcttggtaatctcca | 71 | 32 |
| 109132 | Coding | 1285 | gcaatgagctgtgcaatctg | 80 | 33 |
| 109133 | Coding | 1350 | catatccttccagcccaaag | 52 | 34 |
| 109134 | Coding | 1421 | ccggttgtattgctgctgca | 89 | 35 |
| 109135 | Coding | 1483 | ccagaggctccagagcgcat | 90 | 36 |
| 109136 | Coding | 1549 | tgcatctggccgctggtaat | 48 | 37 |
| 109137 | Coding | 1602 | tggttccagtgagtgcctgc | 83 | 38 |
| 109138 | Coding | 1654 | aagtcatccagggtggcctg | 78 | 39 |
| 109139 | Coding | 1726 | tttgattcatccatcttgtt | 76 | 40 |
| 109140 | Coding | 1781 | caccacagacgcagtaccag | 23 | 41 |
| 109141 | Coding | 1831 | cagcccactgcggtatagtc | 86 | 42 |
| 109142 | Coding | 1885 | agcttcacccacgggacat | 74 | 43 |
| 109143 | Coding | 1948 | cccttgctgcctgcaacag | 48 | 44 |
| 109144 | Coding | 1997 | actggctggttgggcactgc | 73 | 45 |
| 109145 | Coding | 2074 | ccaatttgttgcaacagctc | 85 | 46 |
| 109146 | Coding | 2146 | gctgcagcacttgccacagc | 73 | 47 |
| 109147 | Coding | 2199 | gtcccgagtcctctgtccgc | 71 | 48 |
| 109148 | Coding | 2258 | cactagttgggaagtggata | 37 | 49 |
| 109149 | Coding | 2314 | agttgctcttggcagacagg | 76 | 50 |
| 109150 | Coding | 2373 | cctgggaggcagacacacag | 46 | 51 |
| 109151 | Coding | 2446 | tcatttagggcctgggtgac | 56 | 52 |
| 109152 | Coding | 2515 | tcagtagcctggtcataacg | 65 | 53 |
| 109153 | Coding | 2585 | ggcctgtcccaccatctccc | 76 | 54 |
| 109154 | Coding | 2641 | tcagcatcagccttgatggc | 78 | 55 |
| 109155 | Coding | 2712 | tggctgtggcatcagctagg | 76 | 56 |
| 109156 | Coding | 2770 | tgctgctgctcctcactgtc | 86 | 57 |
| 109157 | Coding | 2832 | tggcattctgcgcagctgca | 84 | 58 |
| 109158 | Coding | 2906 | agcgatggtctgtgtggctg | 76 | 59 |
| 109159 | Coding | 3018 | ggacgccctgcaccagcagt | 86 | 60 |
| 109160 | Coding | 3111 | ccaccatcttcccacctggc | 66 | 61 |
| 109161 | Coding | 3195 | cggtgcccaggttcttggca | 29 | 62 |
| 109162 | Coding | 3273 | cactcagtgcagaatccatc | 59 | 63 |
| 109163 | Coding | 3372 | gggtacacttctccattgtc | 77 | 64 |
| 109164 | Coding | 3441 | cctgggcaacctctcccagt | 57 | 65 |
| 109165 | Coding | 3516 | ccctagcggcctgggccagt | 82 | 66 |
| 109166 | Coding | 3593 | ggccttgtccagcacatcac | 81 | 67 |
| 109167 | Coding | 3709 | ctgacacagcggttcagagc | 77 | 68 |
| 109168 | Coding | 3786 | agtcactcaggagtcgcttg | 69 | 69 |
| 109169 | Coding | 3865 | gctgcctgattcagcccagc | 15 | 70 |
| 109170 | Coding | 3950 | gaaggtgctgaagtcctgtc | 73 | 71 |
| 109171 | Coding | 4033 | gagatgcccttcaagttgga | 2 | 72 |
| 109172 | Coding | 4137 | cagttactgccctggcagct | 73 | 73 |
| 109173 | Coding | 4219 | tccaattcccgcagggcgtt | 71 | 74 |
| 109174 | Coding | 4304 | gttctccattacactgtcca | 6 | 75 |
| 109175 | Coding | 4382 | ggcatctccaaactctggca | 80 | 76 |
| 109176 | Coding | 4550 | caaactctggcaggccatct | 73 | 77 |
| 109177 | Coding | 4685 | tacaaactggcgcttggcag | 74 | 78 |
| 109178 | Coding | 4842 | ggttggacgcaaaggcactc | 83 | 79 |
| 109179 | Coding | 5067 | tgtccctcatgcttgtaatt | 77 | 80 |
| 109180 | Coding | 5216 | cagcatctcagtgtgcaagg | 67 | 81 |
| 109181 | Coding | 6190 | tccaccagcaccttcgcagt | 52 | 82 |
| 109182 | Coding | 6681 | cagcaacggccttggcggtt | 67 | 83 |
| 109183 | Coding | 7195 | gcagcctttaccagtgcact | 75 | 84 |
| 109184 | Coding | 7568 | tgtctcattctcctgctctt | 71 | 85 |
| 109185 | Stop Codon | 7742 | gaggcttctttagtgctcat | 87 | 86 |
| 109186 | 3' UTR | 7757 | ctgcattaaatagaagaggc | 89 | 87 |
| 109187 | 3' UTR | 7790 | ttggtagtggcacgcacagt | 79 | 88 |
| 109188 | 3' UTR | 8012 | cagattcagatcgaggtaca | 84 | 89 |

As shown in Table 1, SEQ ID NOs 11, 12, 13, 14, 15, 16, 17, 18, 19, 21, 22, 24, 25, 26, 27, 28, 29, 30, 31, 32, 33, 34, 35, 36, 38, 39, 40, 42, 43, 45, 46, 47, 48, 50, 52, 53, 54, 55, 56, 57, 58, 59, 60, 61, 63, 64, 65, 66, 67, 68, 69, 71, 73, 74, 76, 77, 78, 79, 80, 81, 82, 83, 84, 85, 86, 87, 88 and 89 demonstrated at least 50% inhibition of Talin expression in this experiment and are therefore preferred.

Example 16

Western Blot Analysis of Talin Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to Talin is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. An antisense compound 16 to 30 nucleobases in length targeted to nucleobases 1 through 19 or nucleobases 73 through 92 of a 5'-untranslated region, nucleobases 157 through 176, nucleobases 198 through 217, nucleobases 257 through 276, nucleobases 320 through 339, nucleobases 361 through 380, nucleobases 419 through 438, nucleobases 460 through 479, nucleobases 503 through 522, nucleobases 572 through 591, nucleobases 635 through 654, nucleobases 707 through 726, nucleobases 768 through 787, nucleobases 824 through 843, nucleobases 887 through 906, nucleobases 943 through 962, nucleobases 998 through 1017, nucleobases 1057 through 1076, nucleobases 1126 through 1145, nucleobases 1181 through 1200, nucleobases 1236 through 1255, nucleobases 1285 through 1304, nucleobases 1350 through 1369, nucleobases 1421 through 1440, nucleobases 1483 through 1502, nucleobases 1549 through 1568, nucleobases 1602 through 1621, nucleobases 1654 through 1673, nucleobases 1726 through 1745, nucleobases 1781 through 1800, nucleobases 1831 through 1850, nucleobases 1885 through 1904, nucleobases 1948 through 1967, nucleobases 1997 through 2016, nucleobases 2074 through 2093, nucleobases 2146 through 2165, nucleobases 2199 through 2218, nucleobases 2258 through 2277, nucleobases 2314 through 2333, nucleobases 2373 through 2392, nucleobases 2446 through 2465, nucleobases 2515 through 2534, nucleobases 2585 through 2604, nucleobases 2641 through 2660, nucleobases 2712 through 2731, nucleobases 2770 through 2789, nucleobases 2832 through 2851, nucleobases 2906 through 2925, nucleobases 3018 through 3037, nucleobases 3111 through 3130, nucleobases 3195 through 3214, nucleobases 3273 through 3292, nucleobases 3372 through 3391, nucleobases 3441 through 3460, nucleobases 3516 through 3535, nucleobases 3593 through 3612, nucleobases 3709 through 3728, nucleobases 3786 through 3805, nucleobases 3865 through 3884, nucleobases 3950 through 3969, nucleobases 4033 through 4052, nucleobases 4137 through 4156, nucleobases 4219 through 4238, nucleobases 4304 through 4323, nucleobases 4382 through 4401, nucleobases 4550 through 4569, nucleobases 4685 through 4704, nucleobases 4842 through 4861, nucleobases 5067 through 5086, nucleobases 5216 through 5235, nucleobases 6190 through 6209, nucleobases 6681 through 6700, nucleobases 7195 through 7214, or nucleobases 7568 through 7587 of a coding region, nucleobases 7742 through 7761 of a stop codon region or nucleobases 7757 through 7776, nucleobases 7790 through 7809, or nucleobases 8012 through 8031 of a 3'-untranslated region of a nucleic acid molecule encoding human Talin (SEQ ID NO: 3), wherein said antisense compound specifically hybridizes with one of said regions and inhibits the expression of human Talin.

2. The antisense compound of claim 1, which is an antisense oligonucleotide.

3. The antisense compound of claim 2, wherein the antisense oligonucleotide is a chimeric oligonucleotide.

4. A composition comprising the antisense compound of claim 1 and a pharmaceutically acceptable carrier or diluent.

5. The composition of claim 4 further comprising a colloidal dispersion system.

6. The composition of claim 4, wherein the antisense compound is an antisense oligonucleotide.

7. The antisense compound of claim 2 wherein the antisense oligonucleotide comprises at least one modified internucleoside linkage.

8. The antisense compound of claim 7, wherein the modified internucleoside linkage is a phosphorothioate linkage.

9. The antisense compound of claim 2, wherein the antisense oligonucleotide comprises at least one modified sugar moiety.

10. The antisense compound of claim 9, wherein the modified sugar moiety is a 2'-O-methoxyethyl sugar moiety.

11. The antisense compound of claim 2, wherein the antisense oligonucleotide comprises at least one modified nucleobase.

12. The antisense compound of claim 11, wherein the modified nucleobase is a 5-methylcytosine.

13. A method of inhibiting the expression of human Talin in human cells or tissues comprising contacting said cells or tissues in vitro with the antisense compound of claim 1 so that expression of human Talin is inhibited.

14. An antisense compound up to 30 nucleobases in length comprising at least a 16-nucleobase portion of SEQ ID NO: 11, 12, 13, 14, 15, 16, 17, 18, 19, 21, 22, 24, 25, 26, 27, 28, 29, 30, 31, 32, 33, 34, 35, 36, 38, 39, 40, 42, 43, 45, 46, 47, 48, 50, 52, 53, 54, 55, 56, 57, 58, 59, 60, 61, 63, 64, 65, 66, 67, 68, 69, 71, 73, 74, 76, 77, 78, 79, 80, 81, 82, 83, 84, 85, 86, 87, 88 or 89 which inhibits the expression of human Talin.

15. The antisense compound of claim 14, which is an antisense oligonucleotide.

16. The antisense compound of claim 15, wherein the antisense oligonucleotide comprises at least one modified internucleoside linkage.

17. The antisense compound of claim 16, wherein the modified internucleoside linkage is a phosphorothioate linkage.

18. The antisense compound of claim 15, wherein the antisense oligonucleotide comprises at least one modified sugar moiety.

19. The antisense compound of claim 18, wherein the modified sugar moiety is a 2'-O-methoxyethyl sugar moiety.

20. The antisense compound of claim 15, wherein the antisense oligonucleotide comprises at least one modified nucleobase.

21. The antisense compound of claim 20, wherein the modified nucleobase is a 5-methylcytosine.

22. The antisense compound of claim 15, wherein the antisense oligonucleotide is a chimeric oligonucleotide.

23. A composition comprising the antisense compound of claim 3 and a pharmaceutically acceptable carrier or diluent.

24. The composition of claim 23 further comprising a colloidal dispersion system.

25. The composition of claim 23, wherein the antisense compound is an antisense oligonucleotide.

26. A method of inhibiting the expression of human Talin in human cells or tissues comprising contacting said cells or tissues in vitro with the antisense compound of claim 14 so that expression of human Talin is inhibited.

* * * * *